(12) United States Patent  
Mears

(10) Patent No.: US 6,280,452 B1
(45) Date of Patent: Aug. 28, 2001

(54) BALLOON ACTUATED LIGATING BAND DISPENSER

(75) Inventor: Eric L. Mears, Duluth, GA (US)

(73) Assignee: Ensurg, Inc., Norcross, GA (US)

( * ) Notice: Subject to any disclaimer, the term of this patent is extended or adjusted under 35 U.S.C. 154(b) by 0 days.

(21) Appl. No.: 09/102,243

(22) Filed: Jun. 22, 1998

(51) Int. Cl.[7] ................................................. A61B 17/10
(52) U.S. Cl. ......................... 606/140; 606/151; 606/139
(58) Field of Search ....................... 604/96.01, 99.02, 604/103, 103.08; 606/139, 140, 143, 144, 148, 151, 157; 600/204, 207, 210

(56) References Cited

U.S. PATENT DOCUMENTS

| 3,760,810 | 9/1973 | Van Hoorn . | |
|---|---|---|---|
| 3,911,923 | 10/1975 | Yoon . | |
| 4,226,239 | 10/1980 | Polk et al. . | |
| 4,257,419 | 3/1981 | Göltner et al. . | |
| 4,990,152 | 2/1991 | Yoon | 606/140 |
| 5,207,690 | 5/1993 | Rohrabacher et al. | 606/135 |
| 5,269,789 | 12/1993 | Chin et al. | 606/140 |
| 5,320,630 | * 6/1994 | Ahmed | 606/140 |
| 5,356,416 | 10/1994 | Chu et al. | 606/140 |
| 5,398,844 | 3/1995 | Zaslavsky et al. . | |
| 5,462,559 | * 10/1995 | Ahmed | 606/140 |
| 5,507,797 | 4/1996 | Suzuki et al. | 606/140 |
| 5,569,268 | 10/1996 | Hosoda | 606/140 |
| 5,624,453 | 4/1997 | Ahmed | 606/140 |
| 5,681,328 | 10/1997 | Lamport et al. | 606/140 |
| 5,697,940 | 12/1997 | Chu et al. | 606/140 |
| 5,735,861 | 4/1998 | Peifer et al. | 606/139 |
| 5,814,062 | * 9/1998 | Sepetka et al. | 606/198 |

OTHER PUBLICATIONS

Directions for Use Brochure for Speedband™ Multiple Band Ligator, Microvasive Boston Scientific Corporation, pp. 1–8, 1995.

* cited by examiner

Primary Examiner—Glenn K. Dawson
(74) Attorney, Agent, or Firm—Sidley Austin Brown & Wood

(57) ABSTRACT

A ligating band dispenser includes a cylindrical inner sleeve and at least a partially encompassing balloon, where the inner sleeve supports one or more expanded ligating bands external to the balloon. This ligating band dispenser allows the introduction of a pressurized fluid between the inner sleeve and the balloon, proximal to a distal-most, stored ligating band, to effect the distal displacement and dispensing of one or more stored ligating bands.

24 Claims, 4 Drawing Sheets

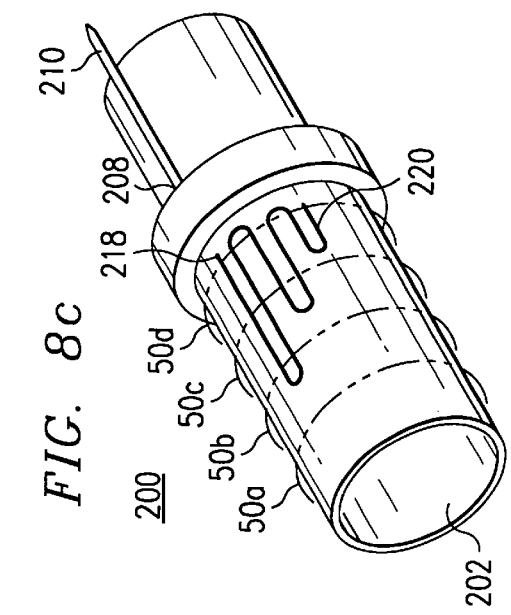
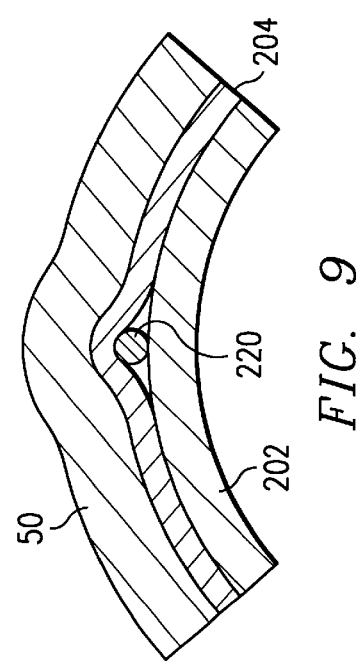
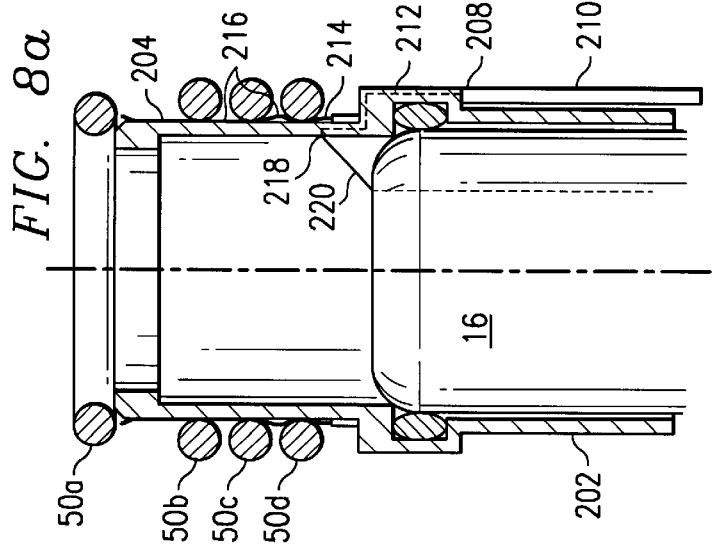
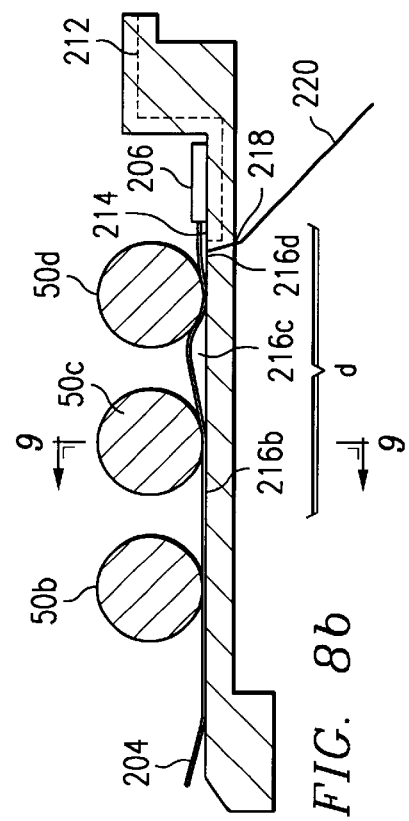

BALLOON ACTUATED LIGATING BAND DISPENSER

BACKGROUND OF THE INVENTION

Ligation is a medical procedure in which, for example, an elastic ligating band, is placed about tissue to prevent fluid flow therethrough. Where a ligating band is placed about, for example, a ballooning varix, polyp, hemorrhoid, or pre-cancerous lesion, a contracted ligating band induces fusion and healing in the base tissue and subjects the ligated tissue to necrosis. The necrotic tissue eventually separates from the surrounding tissue and passes into the human system. Alternatively, ligation may also be used for purposes of sterilization, wherein a ligating band may be placed over a folded loop portion of a Fallopian tube or a vas deferens to prevent the passage of internal reproductive fluids.

Means for delivering ligating bands, or ligating band dispensers, take various forms. One such form is a dedicated ligating band dispenser instrument which has a dispensing portion at a distal end, an actuating mechanism at a proximal end, and a typically rigid shaft therebetween. These instruments are useful for ligating tissue in which the user has access to the tissue to be ligated, e.g., tissue exposed through an invasive surgical procedure.

In contrast, ligating band dispensers may be positioned on the distal tip of an endoscope or a laparoscope. An endoscope is a conventional medical device used for viewing, exploring, and delivering therapies to internal regions of a patient. A laparoscope is a specialized endoscope for viewing a patient's peritoneal cavity. Unlike dedicated ligating band dispensing instruments, an endoscope allows minimally invasive exploration of regions which would otherwise require more significant surgical procedures.

FIGS. 1 and 2 illustrate a conventional endoscope. Endoscope 10 has a control portion 12 and an insertion portion 14 terminating at insertion tip 16. Insertion portion 14 is of such a length to permit access to internal regions of a patient.

FIG. 2 illustrates the face of insertion tip 16. A number of channels extend from the control portion 12 to the insertion tip 16, where the channels terminate in functional outlets 18–26. For the purposes of this example, outlet 18 is a light source; outlet 20 is a wide-field image sensing device, which transmits a video or fiber optic signal to a coupled monitor or eyepiece (not shown) at control portion 12; outlet 22 enables the delivery of a stream of water or air for clearing the image receiving device or flushing an internal bodily region; and outlet 24 is an outlet to a working (or biopsy) channel. Inlet 28 of the working channel can be coupled to a suction device or a lavage fluid source (not shown) or can receive various medical instrumentation (not shown) for passage through the working channel and outlet 24. Optional outlet 26, for larger diameter endoscopes, is an outlet for a second working channel. A second working channel allows additional operations in a manner consistent with the working channel described above.

For a ligation procedure, a ligating band dispenser, mounted on insertion tip 16 of a hosting endoscope 10, is inserted into a patient, for example, through the mouth, to observe certain internal regions. A user navigates the insertion tip 16 in accordance with images produced by the image-sensing device of outlet 20. Once tissue has been targeted for ligation, the distal end of the dispenser is positioned adjacent to the targeted tissue. The user applies a vacuum to the appropriate outlet of insertion tip 16 (e.g., outlet 24), or passes instrumentation (e.g., forceps) through the work channel and outlet 24, to draw the targeted tissue into a volume defined by the inner periphery of the dispenser.

The user then dispenses a ligating band (two dispensers and their dispensing mechanisms are discussed in greater detail below). Upon dispensing a ligating band, the dispensed ligating band attempts to assume its non-expanded dimensions. As the subject tissue is positioned within the inner periphery of the ligating band, constriction of the band effectively ligates the subject tissue. The applied suction is ceased, and the insertion tip 16 is moved away from the ligated tissue and further exploration may be undertaken, if necessary.

Conventional endoscope ligating band dispensers commonly employ dispensing mechanisms which unnecessarily complicate a ligating procedure. Two examples of conventional mechanisms include a dispenser having a plurality of draw strings 1002 which are individually coupled to each of the stored ligating bands 1000 (FIG. 3), and a dispenser having a mechanically actuated housing which engages and requires movement of all stored ligating bands 1000 for each dispensing operation (FIG. 4).

In reference to FIG. 3, draw strings 1002 extend from each ligating band 1000 and around the distal end of the dispenser before extending proximally through the work channel of a receiving endoscope 10. Application of a proximally-directed force to a single draw string 1002 effects distal movement and dispensing of a coupled ligating band 1000.

As shown, each ligating band 1000 must be individually and properly coupled to at least one draw string 1002 to allow band control. As the number of stored ligating bands 1000 increase, the number of draw strings 1002, and the criticality of their placement, increases. The draw strings 1002 must be optimally positioned to ensure reliable dispensing of a distal-most ligating band, to avoid obstruction of the image sensing device of the hosting endoscope, and to avoid filling the volume defined by the dispenser and effectively decreasing the tissue capacity of the dispenser. Understandably, the construction of this dispenser requires considerable care and is necessarily labor intensive.

Referring to FIG. 4, another conventional dispenser example includes a mechanically actuated housing having a movable inner element 1008 and a fixed outer element 1010. Outer element 1010 carries a plurality of expanded ligating bands 1000, excepting the distal-most ligating band 1000a, which is carried by inner element 1008. For dispensing ligating band 1000a, element 1008 is drawn proximally, causing the distal-most ligating band 1000a to be released when inner element 1008 is pulled within outer element 1010. During such movement, the remaining ligating bands 1000 are displaced by shoulders 1012 so that when inner element 1008 returns distally, ligating bands 1000 are distally advanced.

This dispenser requires an applied dispensing force having a magnitude sufficient to not only dispense a single ligating band but also distally displace the remaining stored ligating bands in preparation for a next ligation. As the number of stored ligating bands increase, the force necessary to move the ligating bands as a group also increases. Consequently, a user may experience some level of awkwardness during a procedure due to the force which may be necessary to dispense one or more ligating bands. Of further concern, this dispenser requires a number of working components to effect the dispensing of a ligating band, thus likely increasing the costs of the dispenser (i.e., assembly and materials) and functionally increasing the opportunity for a device malfunction.

Consequently, a need exists for a simple ligating band dispenser which offers safe, reliable, cost effective delivery of multiple ligating bands.

SUMMARY OF THE INVENTION

The present invention is directed to a ligating band dispenser. According to one aspect of the present invention, a ligating band dispenser is provided with an inner member and a flexible member receiving and at least partially encompassing the inner member. The relative positioning of the inner member to the flexible member defines a space therebetween. The dispenser further includes at least one fluid lumen which has an outlet in fluid communication with the space.

Accordingly to another aspect of the present invention, the above dispenser includes a valve mechanism. The valve mechanism enables the selective distribution of pressurized fluid, delivered through the at least one fluid lumen, to substantially discrete portions of the space defined by the flexible member and the inner member.

In operation, a ligating procedure utilizing such a dispenser would generally include at least positioning a ligating band dispenser of the above description on a distal end of an insertion portion of an endoscope. The ligating band dispenser should support at least one ligating band, and its at least one fluid lumen should be in fluid communication with a pressurized fluid source. The insertion portion, including the dispenser, is then inserted into a patient and navigated to a desired tissue site. Adjacent to the tissue site, tissue which is to be ligated is drawn within a volume defined by the dispenser. Pressurized fluid is delivered from the source to the at least one lumen to dispense a ligating band.

An object of the present invention is to provide a ligating band dispenser having simple, accurate functionality to independently and sequentially dispense one or more ligating bands.

Another object of the present invention is to provide a ligating band dispenser having a minimal number of working components to effect the dispensing of a ligating band.

Another object of the present invention is to provide a ligating band dispenser which dispenses a stored ligating band through controlling delivery of a pressurized fluid.

Other objects and advantages of the present invention will be apparent to those of ordinary skill in the art having reference to the following specification together with the drawings.

BRIEF DESCRIPTION OF THE DRAWINGS

Referring now to the drawings in which like reference numerals and letters indicate corresponding elements throughout the several views, if applicable:

FIGS. 8a and 8b are partial sectional views of a third embodiment of the dispenser of FIG. 5;

FIG. 8c is a perspective view of an alternative configuration of the third embodiment of FIGS. 8a and 8b;

FIG. 9 is a partial, cross-sectional view along line 9—9 of FIG. 8b;

DETAILED DESCRIPTION OF THE PREFERRED EMBODIMENTS

Figure 1:
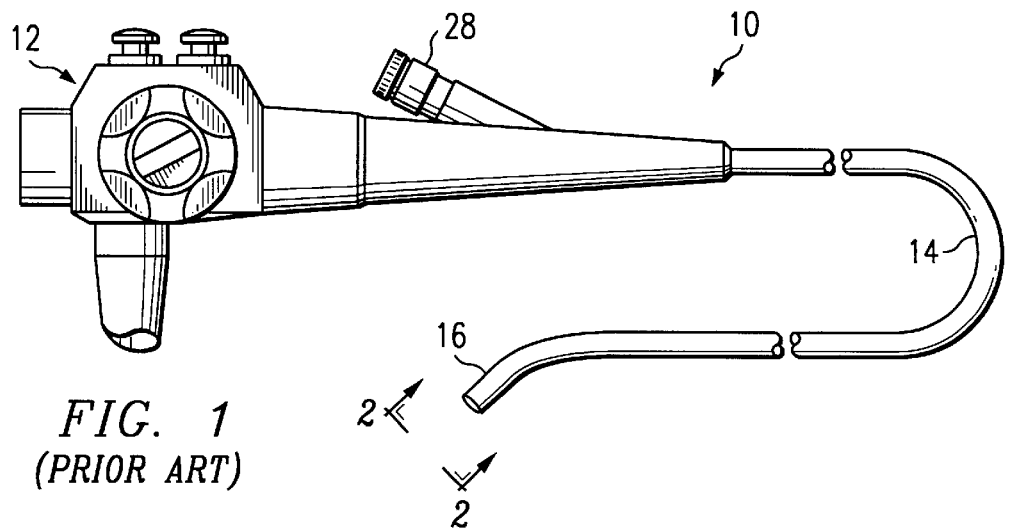
FIG. 1 illustrates a conventional endoscope device.
Figure 2:
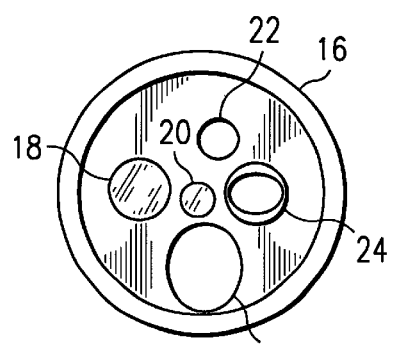
FIG. 2 is a view along line 2—2 of the insertion tip of the endoscope device of FIG. 1.
Figure 3:
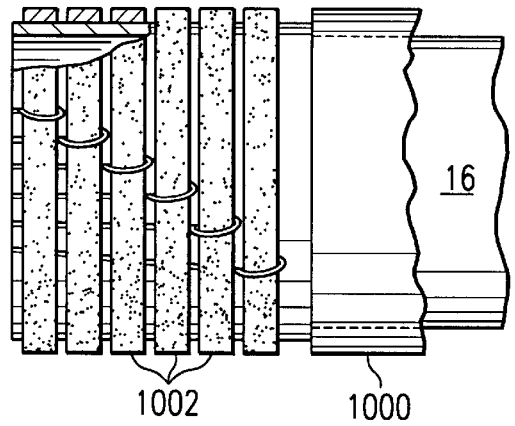
FIG. 3 illustrates a conventional ligating band dispenser.
Figure 4:
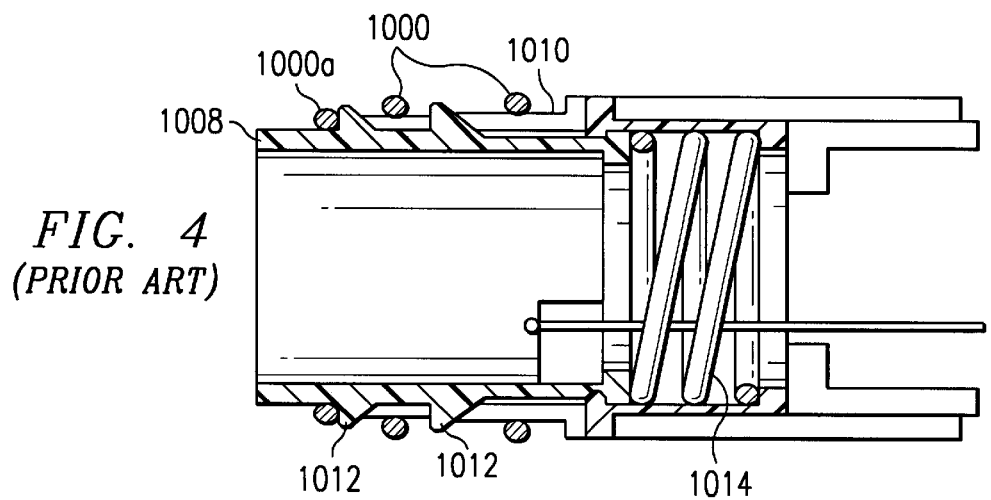
FIG. 4 illustrates a conventional ligating band dispenser.
Figure 5:
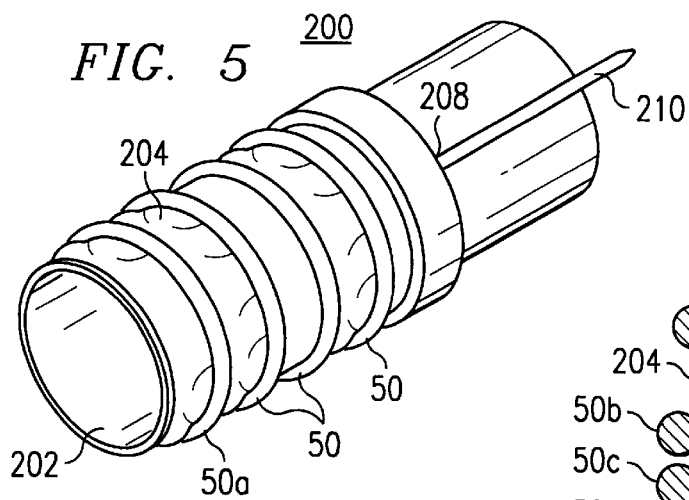
FIG. 5 is a perspective view of a ligating band dispenser in accordance with the present invention.
Figure 11:
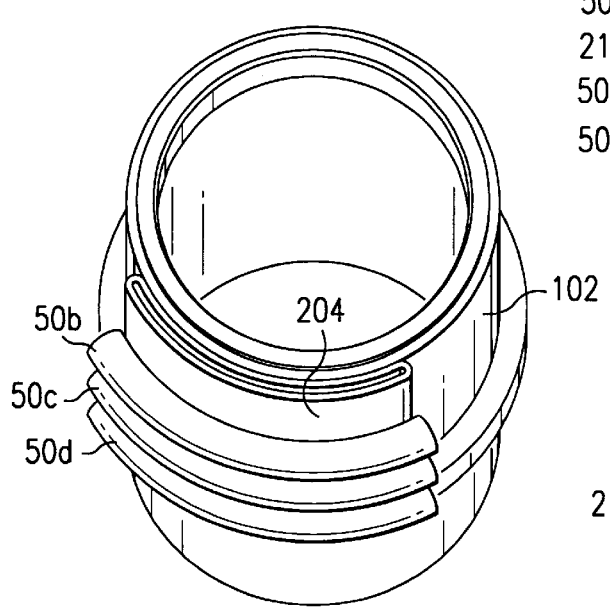
FIG. 11 is a perspective view of another configuration of the dispenser of FIG. 5.

FIG. 5 illustrates ligating band dispenser 200. Dispenser 200 generally includes sleeve 202 and an at least partially encompassing thin flexible, fluid-impermeable balloon positioned about a distal end of sleeve 202. The proximal end of balloon (or membrane) 204 is secured to sleeve 202, where a hermetic seal 206 is established between sleeve 202 and balloon 204. Where balloon 204 is largely cylindrical, a proximal, circumferential seal 206 is formed. Alternatively, where balloon 204 extends only about some arcuate portion of sleeve 202, seal 206 should preferably be formed along all but the distal edge of the balloon 204, or balloon 204 may be a continuous member which overlaps itself for the arcuate portion of sleeve 202 (FIG. 11) and, if desired, permits sealing only along its proximal end. Seal 206 may be established through bonding sleeve 202 to balloon 204 and/or placing a band (FIGS. 7b and 8b) about balloon 204 to tightly secure balloon 204 to sleeve 202.

In a first embodiment, sleeve 202 includes fluid inlet 208. Fluid inlet 208 receives multi-lumen tube 210 and is in fluid communication with fluid lumens 212a–212d. Tube 210 delivers a pressurized fluid, for example, air, water, or saline, to fluid lumens 212a–212d from a pressurized fluid source (not shown) at or about control portion 12 of a hosting endoscope 10. For this embodiment, tube 210 runs external to insertion portion 14 of the hosting endoscope 10; however, a functionally equivalent pressurized fluid lumen may be provided by any one of the appropriate lumen of insertion portion 14 of an endoscope 10.

Fluid inlet 208 individually accommodates the multiple lumens of tube 210, where each lumen of tube 210 is exclusively coupled to a corresponding lumen of fluid lumens 212a–212d. In this example, fluid lumens 212a–212d are formed within the walls of sleeve 202 and progressively extend distally from fluid inlet 208. Alternatively, an additional element (not shown) may be joined to the inner periphery of sleeve 202, where channels are formed along a surface which is joined to sleeve 202. The relationship between the additional element and the sleeve 202 form fluid lumens 212a–212d. For either variation, fluid lumen 212d extends distally from fluid inlet 208 for a first distance, fluid lumen 212c extends distally beyond fluid lumen 212d, fluid lumen 212b extends distally beyond fluid lumen 212c, and fluid lumen 212a extends to a distal-most point. Each fluid lumen respectfully terminates at orifices 214a–214d, which extend from an outer periphery of sleeve 202 to their respective fluid lumens 212a–212d.

Expanded ligating bands 50 are positioned about sleeve 102 and external to balloon 204. Stored ligating bands 50 subdivide a space defined between sleeve 202 and balloon 204 into discrete chambers 216, where the circumferential constriction of each expanded ligating band 50 forms a transient seal between sleeve 202 and balloon 204. It is preferred that ligating bands 50 are spaced along the length of sleeve 202 so that at least one orifice 214x is positioned between each ligating band 50 (or ligating band 50 and seal 206) and is in fluid communication with each chamber 216.

Figure 6:
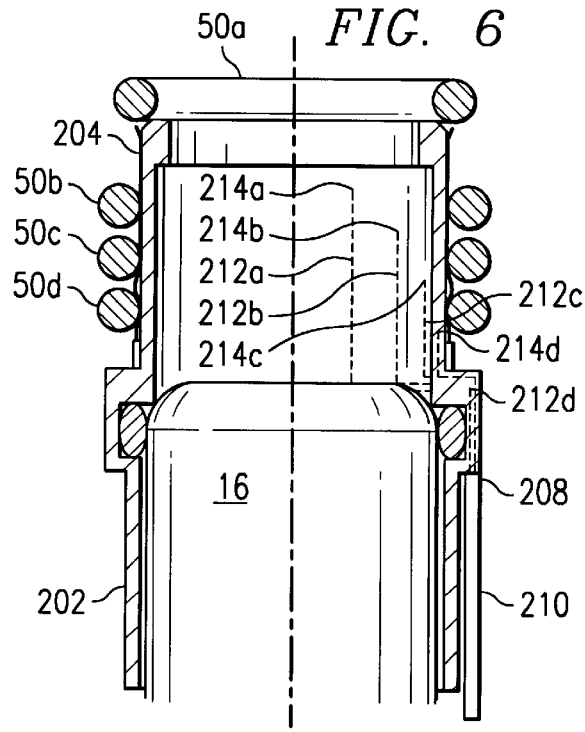
FIG. 6 is a partial sectional view of a first embodiment of the dispenser of FIG. 5.

For a dispensing operation, a distal-most ligating band 50 may be dispensed through the pressurization of a chamber 216 proximal to the distal-most ligating band 50. As an example, and in reference to FIG. 6, pressurized fluid is directed through orifice 214b to pressurize that chamber 216 immediately proximal to ligating band 50b. As pressure within chamber 216 increases, ligating band 50b is caused to displace distally. Distal movement of stored ligating bands 50 may occur through rolling, sliding, or some combination thereof, depending on the material and geometry of ligating band 60 and/or the lubrication present. When ligating band 50b passes orifice 214a, pressurized fluid is directed through orifice 214a to maintain distal movement of ligating band 50b to a release position.

As illustrated by this example, the material of balloon 204 should balance competing performance requirements, where balloon 204 should have a sufficient durometer to prevent excessive ballooning when subjected to pressurization, but balloon 204 must also allow the formation of a driving annular surface wave suitable for initiating and maintaining the distal movement of ligating bands 50.

As an alternative to inlet 208 coupling each lumen of multi-lumen tube 210 to a respective fluid lumen of lumens 212a–212d, a valve mechanism (not shown) may be provided to selectively direct pressurized fluid from a single lumen tube 210 to each lumen of lumens 212a–212d.

Figure 7A:
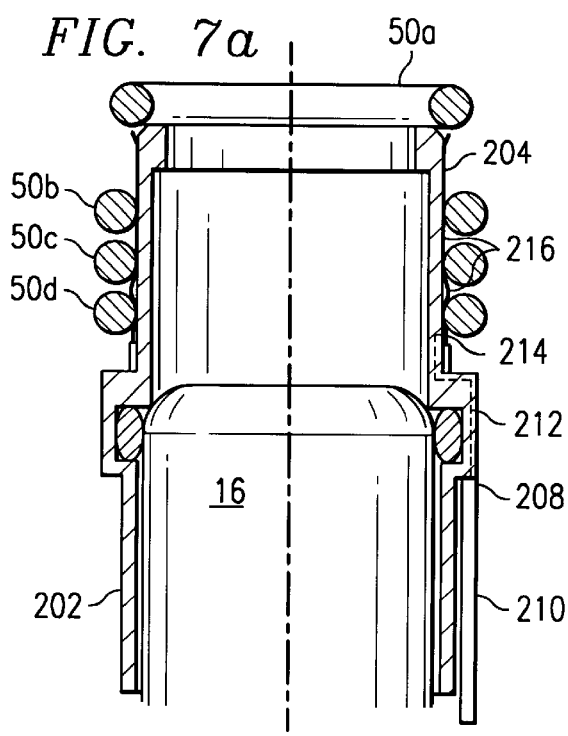
FIGS. 7a and 7b are partial sectional views of a second embodiment of the dispenser of FIG. 5.
Figure 7B:
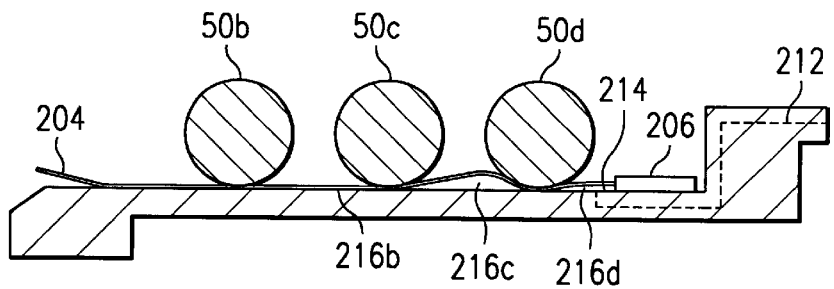

FIGS. 7a and 7b illustrate a second embodiment of dispenser 200, wherein like elements maintain like references. For this embodiment, sleeve 202 has only a single fluid lumen 212 having an orifice 214 positioned between seal 206 and a proximal-most ligating band 50d.

Referring to FIG. 7b, to dispense a distal-most ligating band 50b, a pressurized fluid is introduced through orifice 214. As pressure in chamber 216d reaches a predetermined level (where the predetermined level is a function of the circumferential force applied by ligating bands 50 and the material characteristics of balloon 204) ligating band 50d is caused to displace in a manner to release the transient seal established by ligating band 50d and allow pressurization of chamber 216c. Displacement of ligating band 50d is limited to that which occurs prior to an equalization of pressure in chamber 216c and chamber 216d. This process of chamber pressurization continues with the pressurization of chamber 216b. As pressure increases in chamber 216b, ligating band 50b will displace, allowing the pressurized fluid to escape to atmospheric conditions distal to ligating band 216b. As the pressure proximal to and distal to ligating band 50b is imbalanced, ligating band 50b is advanced distally to a dispensing point.

Figure 10A:
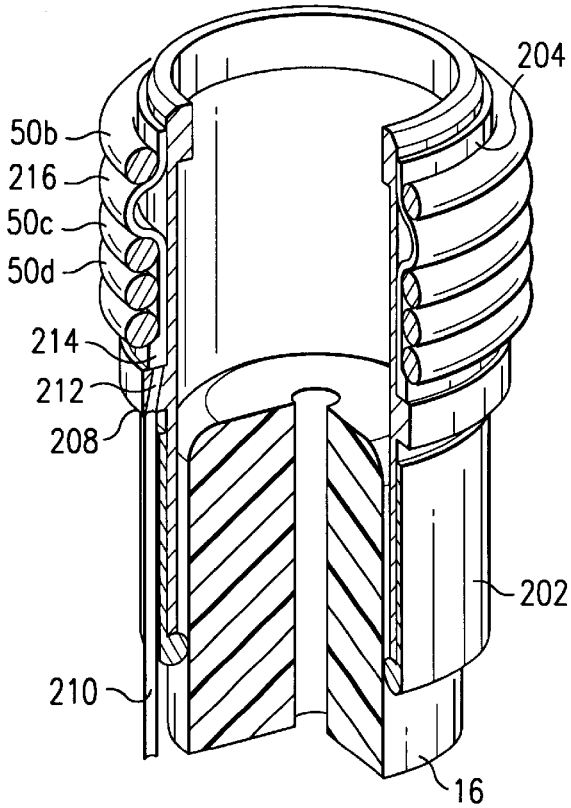
FIG. 10a is a perspective, partial sectional view of an alternative configuration of the dispenser of FIGS. 7a and 7b.

FIG. 10a illustrates an alternative configuration for the second embodiment. Specifically, a seal between sleeve 202 and insertion tip 16 is relocated proximally, thus enabling a direct fluid lumen 212 to be formed in a portion of sleeve 202. As shown in FIG. 10a, fluid lumen 212 opens into that space between balloon 204 and sleeve 202, where balloon 204 is attached to sleeve 202 to permit fluid communication through fluid lumen 212 to that space between sleeve 202 and balloon 204. For the alternative embodiment of FIG. 11, fluid lumen 212 opens into a space defined by balloon 204.

FIGS. 8a and 8b illustrate a modification of the second embodiment of dispenser 200. In addition to the configuration described above, dispenser 200 includes filament 220. Filament 220 extends from the outer periphery of member 202 to the volume defined by member 202 through aperture 218. It is preferred that aperture 218 be positioned generally adjacent to orifice 214 of fluid lumen 212. Alternatively, filament 220 may pass through fluid lumen 212.

Filament 220 is a valve mechanism to direct pressurized fluid to a selected chamber 216x. Filament 220 originates at control portion 12 of a hosting endoscope 10, extends through tube 210 (or a lumen of insertion portion 14 and aperture 218), to lie along the exterior periphery of sleeve 202 in a direction largely parallel to a longitudinal axis of sleeve 202. For the purposes of the example illustrated in FIG. 8b, filament 220 initially extends for distance d into chamber 216b.

For a dispensing operation, and in further reference to FIG. 8b, a pressurized fluid is introduced into chamber 216d. Filament 220 directs the delivered pressurized fluid to chamber 216b, which is immediately proximal to ligating band 50b, by disrupting each seal (see FIG. 9) formed between sleeve 202 and balloon 204 by the circumferential constriction of each ligating band 50. Increasing pressure within chamber 216b effects distal movement of ligating band 50b to a dispensing position. Following dispensing of ligating band 50b, filament 220 is withdrawn proximally until a distal end of filament 220 is within chamber 216c.

The effective nominal distance between chamber 216b and chamber 216c is a function of the expanded cross-sectional diameter of ligating band 50c and/or the spacing between ligating bands 50b and 50c. This effective nominal distance is approximately 1–2 mm. Consequently, moving filament 220 from one chamber 216x to the next requires a high degree of precision.

To provide a user greater control over the valve mechanism, filament 220 may be wound about the exterior periphery of sleeve 202 in a prescribed pattern. As one example, FIG. 8c illustrates a looped configuration of filament 220 which results in filament 220 extending beneath each proximal ligating bands 50 two or more times. In addition to improving control over the valve mechanism, this configuration further increases the flow path around the filament 220 and thereby the pressurization response time for pressure equalization in each of the affected chambers 216x during a dispensing operation.

Figure 10B:
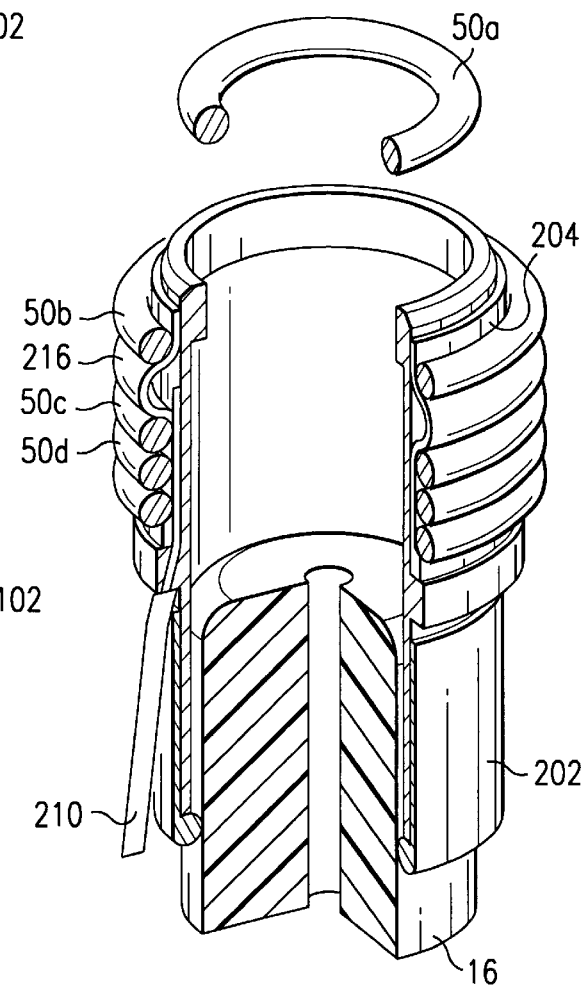
FIG. 10b is a perspective, partial sectional view of an alternative configuration of the dispenser of FIGS. 8a and 8b.

As an alternative to filament 220, tube 210 may be slidably engaged by a portion of sleeve 202, thus allowing tube 210 to perform the same function as filament 220 by directly delivering pressurized fluid to a distal-most chamber 216x. More preferably, tube 210 may carry a movable extension of tube 210, which itself initially extends along sleeve 202 and may be retracted along sleeve 202 to sequentially dispense stored ligating bands 50. Referring to FIG. 10b to illustrate the functionality of the movable extension of tube 210, the distal end of the movable extension of tube 210 is initially positioned just proximal to a distal-most ligating band 50b. After ligating band 50b is dispensed, the extension of tube 210 is retracted proximally to a position proximal to the then distal-most ligating band 50c.

For the above examples, ligating band dispenser 200 is shown to be fixed on an insertion tip 16 of a hosting endoscope 10. As an alternative embodiment, dispenser 200 may be adapted to move relative to an insertion tip 16 of a hosting endoscope 10 and controlled in accordance with that disclosed within co-pending application, Ser. No. 09/062,281, filed Apr. 17, 1998.

Ligating band dispenser 200 may be further used with an endoscope, as illustrated in the above examples, or manufactured or included as part of a dedicated ligating instrument (not shown).

While the invention has been described herein relative to a number of particularized embodiments, it is understood that modifications of, and alternatives to, these embodiments, such modifications and alternatives realizing the advantages and benefits of this invention, will be apparent to those of ordinary skill in the art having reference to this specification and its drawings. It is contemplated that such modifications and alternatives are within the scope of this invention as subsequently claimed herein, and it is intended that the scope of this invention claimed herein be limited only by the broadest interpretation of the appended claims to which the inventors are legally entitled.

What is claimed is:

1. A ligating band dispenser comprising:

an inner member;

a balloon, having a proximal portion and a distal portion, receiving and at least partially encompassing the inner member, wherein the inner member supports the balloon; and at least one lumen having an outlet that opens into a space radially between the inner member and the balloon, wherein the balloon is secured to the inner member, at least in part, via a fixed seal proximal to the outlet.

2. A dispenser in accordance with claim 1, wherein the distal portion of the balloon is open.

3. A ligating band dispenser comprising:

an inner member;

a flexible member receiving and at least partially encompassing the inner member, wherein the inner member supports the flexible member and a space is defined radially between the inner member and the flexible member; and at least one lumen having an outlet in fluid communication with the space;

a fixed seal, positioned proximal to the outlet, that defines a proximal boundary of the space, wherein the fixed seal operatively prevents passage of fluid proximal to the fixed seal when such a fluid is delivered to the space, wherein the inner member is adapted to support at least one ligating band, and wherein in an operative state, a supported ligating band is positionable external to the flexible member and distal to the fixed seal so as to establish a transient seal between the inner sleeve and the flexible member.

4. A dispenser in accordance with claim 3, wherein the fixed seal extends between the inner member and the flexible member.

5. A dispenser in accordance with claim 3, wherein when the inner member supports M ligating bands, transient seals established by the M ligating bands effectively segregate the space into M chambers.

6. A dispenser in accordance with claim 5, wherein each chamber of the M chambers is adapted to be at least initially in fluid communication with at least one outlet of the at least one lumen to enable chamber pressurization, and wherein pressurization exceeding a prescribed level effects distal advancement of at least a distal, supported ligating band.

7. A dispenser in accordance with claim 3, wherein the dispenser has a plurality of lumens having a corresponding plurality of outlets in fluid communication with the space.

8. A dispenser in accordance with claim 7, wherein the plurality of outlets are formed in an outer periphery of the inner member, and the plurality of outlets are arranged between the fixed seal and a distal end of the flexible member.

9. A ligating band dispenser comprising:

an inner member;

a balloon encompassing the inner member and defining a space radially therebetween, wherein a proximal end of the balloon is sealingly secured to the inner member;

at least one lumen having an outlet in fluid communication with the space; and a valve mechanism to control a distribution of fluid, which is delivered to the space through the at least one lumen, between the balloon and the inner member.

10. A dispenser in accordance with claim 9, wherein the inner member is adapted to support at least one ligating band, external to the balloon and distal to the seal, and when the inner member supports at least one ligating band the space is effectively divided into substantially discrete chambers by each ligating band supported by the inner member, whereas such chambers are established between adjacent ligating bands and between the seal and a ligating band.

11. A dispenser in accordance with claim 10, wherein the valve mechanism is adapted to distribute fluid delivered through the at least one lumen to a predetermined chamber when the inner member supports at least two ligating bands.

12. A dispenser in accordance with claim 11, wherein the valve mechanism includes a filament adapted to prevent formation of fully discrete chambers.

13. A dispenser in accordance with claim 11, wherein the at least one lumen is moveable and can move at least in a direction parallel to a longitudinal axis of the dispenser.

14. A dispenser in accordance with claim 13, wherein the valve mechanism facilitates movement of the moveable lumen to selectively deliver pressurized fluid to at least a predetermined chamber.

15. A dispenser in accordance with claim 10, wherein the outlet of the at least one lumen is in fluid communication with a chamber when the inner member supports at least one ligating band.

16. A dispenser in accordance with claim 9, wherein the dispenser has a plurality of fluid lumens having a corresponding plurality of outlets in fluid communication with the space.

17. A dispenser in accordance with claim 16, wherein the plurality of outlets are formed in an outer periphery of the inner member, and the plurality of outlets are distributed between the seal and a distal end of the balloon.

18. A method of ligating tissue, comprising the steps of:

positioning a ligating band dispenser supporting at least one expanded ligating band on a distal end of an insertion portion of an endoscope, said dispenser including:

an inner member;

a flexible member receiving and at least partially encompassing the inner member, wherein a space is defined between the inner member and the flexible member; and at least one lumen having an outlet in fluid communication with the space, wherein the at least one lumen is selectively coupled to a pressurized fluid source;

inserting the insertion portion, including the dispenser, within a patient;

navigating the insertion portion to a desired tissue site;

adjacent to the tissue site, drawing that tissue to be ligated within a volume defined by the dispenser; and delivering a pressurized fluid from the fluid source to the at least one lumen to dispense a ligating band.

19. A method in accordance with claim 18, wherein the dispenser has a plurality of fluid lumens having a corresponding plurality of outlets in fluid communication with the space.

20. A method in accordance with claim 19, wherein the plurality of outlets are arranged according to the at least one ligating band supported on the inner sleeve.

21. A method in accordance with claim 20, wherein the step of delivering a pressurized fluid further includes delivering a pressurized fluid to a selected outlet and sequentially delivering a pressurized fluid to each outlet distal to the selected outlet to effect and continue distal movement of a ligating band from a position distal to the selected outlet to a dispensing point.

22. A ligating band dispenser comprising:

an inner member;

a flexible member, having a proximal end and a distal end, that receives and at least partially encompasses the inner member, whereas the inner member supports the flexible member and a space is defined between the inner member and the flexible member; and at least one lumen having an outlet, whereas the at least one lumen is in fluid communication with the space, wherein the flexible member is secured to the inner member via a fixed seal proximal to the outlet, and wherein the space is open to an ambient environment via an opening between the distal end of the flexible member and the inner member.

23. A ligating band dispenser comprising:

an inner member;

a flexible member, having an interior surface and an exterior surface, that at least partially encompasses the inner member; and at least one lumen, having an outlet, to deliver a driving fluid, wherein the inner member (i) supports the flexible member through contact with a portion of the exterior surface of the flexible member and (ii) is adapted to support at least one ligating band, external to the flexible member, wherein the interior surface of the flexible member substantially defines a space to receive a driving fluid from the at least one lumen, whereas the outlet of the at least one lumen is in fluid communication with the space.

24. A ligating band dispenser in accordance with claim 23, wherein the flexible member has a generally tubular shape.

* * * * *